(12) United States Patent
Berard-Andersen et al.

(10) Patent No.: US 9,211,106 B2
(45) Date of Patent: Dec. 15, 2015

(54) COUPLING AN ULTRASOUND PROBE TO THE SKIN

(71) Applicant: NeoRad AS, Oslo (NO)

(72) Inventors: Nicolay Berard-Andersen, Oslo (NO); Gjermund Fjeld Olsen, Oslo (NO)

(73) Assignee: NEORAD AS, Oslo (NO)

( * ) Notice: Subject to any disclaimer, the term of this patent is extended or adjusted under 35 U.S.C. 154(b) by 0 days.

(21) Appl. No.: 14/475,596

(22) Filed: Sep. 3, 2014

(65) Prior Publication Data

US 2015/0018686 A1    Jan. 15, 2015

Related U.S. Application Data

(63) Continuation of application No. 13/642,865, filed as application No. PCT/GB2011/000634 on Apr. 21, 2011, now abandoned.

(60) Provisional application No. 61/329,126, filed on Apr. 29, 2010.

(30) Foreign Application Priority Data

Apr. 29, 2010    (GB) .................................. 1007243.7

(51) Int. Cl.
*A61B 8/00*    (2006.01)
*C09J 183/00*    (2006.01)
*C08J 5/00*    (2006.01)
*C09J 7/04*    (2006.01)

(52) U.S. Cl.
CPC .............. *A61B 8/4236* (2013.01); *A61B 8/4281* (2013.01); *A61B 8/4444* (2013.01); *A61B 8/4483* (2013.01); *C08J 5/00* (2013.01); *C09J 7/041* (2013.01); *C09J 183/00* (2013.01); *C08J 2383/00* (2013.01); *Y10T 428/2852* (2015.01); *Y10T 442/674* (2015.04)

(58) Field of Classification Search
CPC ... C09J 183/04; A61B 8/4444; A61B 8/4483; A61B 8/4236; A61B 8/4281
See application file for complete search history.

(56) References Cited

U.S. PATENT DOCUMENTS 4,556,066 A    12/1985   Semrow
4,950,148 A    8/1990   Nakanishi (Continued)

FOREIGN PATENT DOCUMENTS

DE    3936162 A1    6/1991
EP    1318551 A2    6/2003

(Continued)

OTHER PUBLICATIONS

Silbione® RT Gel 4512 A&B data sheet from Bluestar Silicones, Jul. 2009.*

(Continued)

*Primary Examiner* — Margaret Moore
(74) *Attorney, Agent, or Firm* — Sutherland Asbill & Brennan LLP

(57) ABSTRACT

A tape for securing an ultrasound probe to the skin may include a sonolucent silicone gel for transmitting ultrasound from an ultrasound transducer to the body. A method of manufacturing an adhesive silicone product may include a step of treating the adhesive composition or components of the composition to remove air or prevent the formation of air bubbles, in order to provide a sonolucent adhesive product.

10 Claims, 4 Drawing Sheets

(56) References Cited

U.S. PATENT DOCUMENTS

| | | | |
|---|---|---|---|
| 5,011,393 A | 4/1991 | Nakanishi | |
| 5,308,887 A | 5/1994 | Ko et al. | |
| 5,394,877 A | 3/1995 | Orr et al. | |
| 5,656,763 A | 8/1997 | Flax | |
| 6,743,515 B1 | 6/2004 | Muller et al. | |
| 6,846,508 B1 * | 1/2005 | Colas et al. | 427/2.31 |
| 7,211,060 B1 | 5/2007 | Talish et al. | |
| 7,694,570 B1 | 4/2010 | Dam et al. | |
| 8,414,494 B2 | 4/2013 | Vaezy et al. | |
| 2002/0087123 A1 | 7/2002 | Hossainy et al. | |
| 2002/0103433 A1 | 8/2002 | Muramatsu | |
| 2002/0138080 A1 | 9/2002 | Chon | |
| 2004/0035208 A1 | 2/2004 | Diaz et al. | |
| 2005/0075572 A1 | 4/2005 | Mills et al. | |
| 2005/0261588 A1 | 11/2005 | Makin et al. | |
| 2006/0020778 A1 | 1/2006 | Edrington et al. | |
| 2006/0106311 A1 | 5/2006 | Lo et al. | |
| 2007/0016053 A1 | 1/2007 | Lo et al. | |
| 2007/0071707 A1 | 3/2007 | Buchalter | |
| 2007/0244398 A1 | 10/2007 | Lo et al. | |
| 2007/0266792 A1 | 11/2007 | Oosawa | |
| 2008/0312533 A1 * | 12/2008 | Balberg et al. | 600/437 |
| 2009/0142741 A1 | 6/2009 | Ault et al. | |
| 2009/0162596 A1 | 6/2009 | Rios et al. | |
| 2010/0076315 A1 | 3/2010 | Erkamp et al. | |

FOREIGN PATENT DOCUMENTS

| | | |
|---|---|---|
| GB | 698795 A | 10/1953 |
| JP | 57097300 A | 6/1982 |
| JP | 1099535 A | 4/1989 |
| JP | 03151942 A | 6/1991 |
| JP | 7322393 A | 12/1995 |
| WO | 2004/049951 A1 | 6/2004 |
| WO | 2004/052431 A1 | 6/2004 |
| WO | 2007/057826 A1 | 5/2007 |
| WO | 2008/042559 A2 | 4/2008 |
| WO | 2009/044151 A1 | 4/2009 |

OTHER PUBLICATIONS

Silbione® RT Gel 4512 A&B data sheet from Bluestar Silicones, Apr. 2012.*

Silbione® RT Skin Adhesive Series data sheet from Bluestar Silicones, Apr. 2012.*

"The Silbione Difference, Silicones for Healthcare Applications", from Bluestar Silicones, 2009.*

* cited by examiner

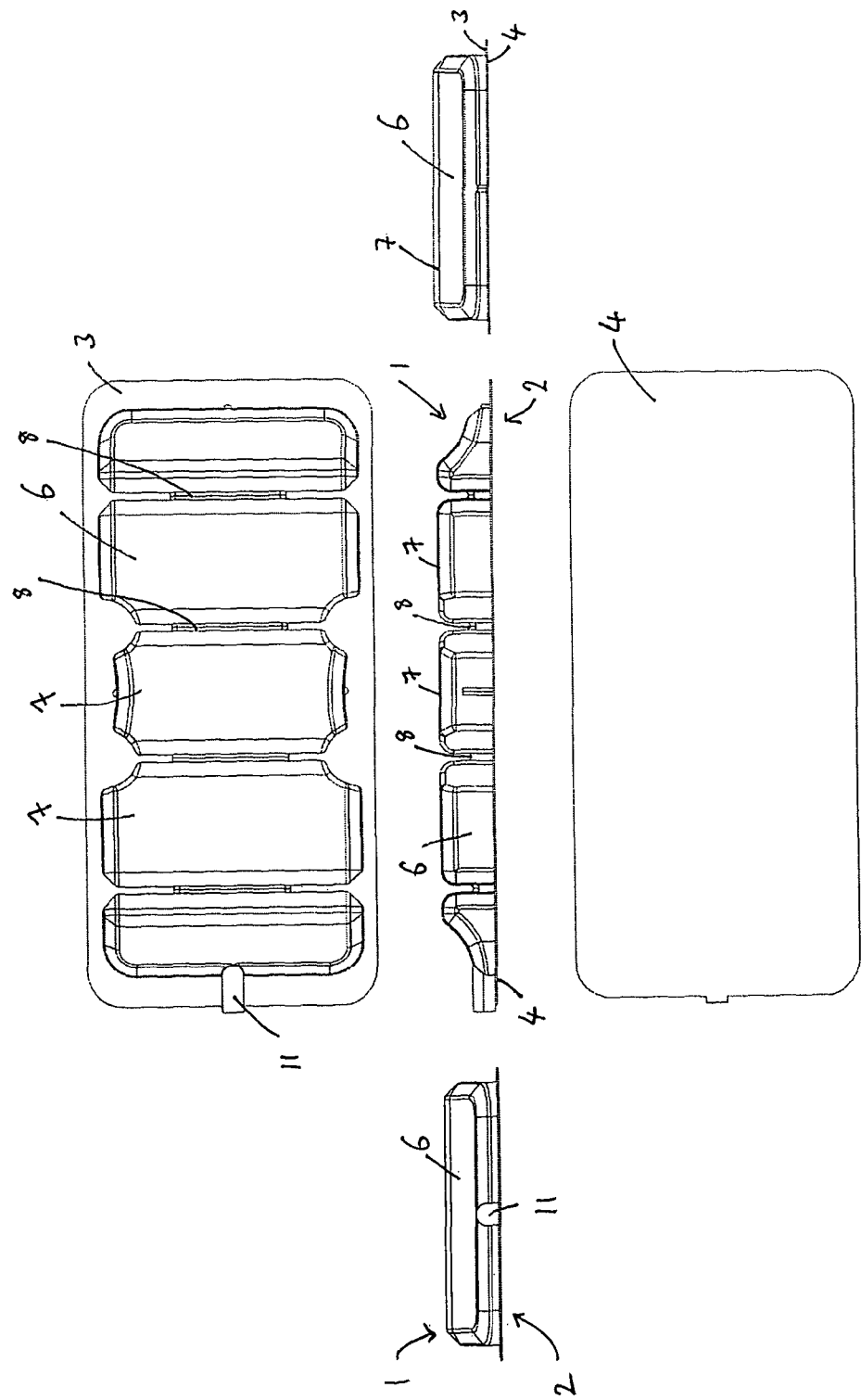

COUPLING AN ULTRASOUND PROBE TO THE SKIN

RELATED APPLICATIONS

The present application is a continuation of U.S. patent application Ser. No. 13/642,865, filed on Nov. 16, 2012, now abandoned. U.S. patent application Ser. No. 13/642,865 is incorporated herein by reference in full.

TECHNICAL FIELD

The invention concerns devices and products for securing an ultrasound probe to the skin, and to related methods of manufacture.

BACKGROUND OF THE INVENTION

Ultrasound imaging or ultrasonography is an ultrasound-based diagnostic imaging technique used to visualize subcutaneous body structures including tendons, muscles, joints, vessels and internal organs for possible pathology or lesions. Obstetric sonography is commonly used during pregnancy and is widely recognized by the public. Various other diagnostic and therapeutic applications are practiced in medicine.

In order to obtain a good quality image of the body structures of interest, it is necessary for the pulses of sound emitted by an ultrasound transducer to be passed into the body and received from the body without interference. The materials that form the face of the transducer are chosen to enable the sound to be transmitted efficiently into the body. In addition, a water-based gel (hydrogel) is placed between the patient's skin and the probe to ensure good acoustic coupling. The gel allows the probe to be moved over the skin whilst maintaining the desired acoustic coupling so that different areas can be imaged as required.

In recent times, a number of innovative applications for ultrasound imaging have been developed where it is desirable to fix an ultrasound probe in a single position for a sustained period of time. WO 2004/052431 and WO 2009/044151 disclose the use of an ultrasound Doppler technique to monitor an injection and provide a signal to indicate the possibility of extravasation. The ultrasound Doppler probe is located in a single position over a vein. WO 2004/049951 discloses a respiration monitoring apparatus where an array of ultrasound transducers is located over the diaphragm. With this apparatus, the acoustic impedance of the tissue adjacent to each transducer is used to determine the presence of aerated and non-aerated tissue, and the degree of lung inspiration is thereby determined. In these applications there is a need to secure the ultrasound probe to the skin.

In addition to securing an ultrasound probe in a single position, it is highly desirable to be able to do this in such a way that all transducers in the probe, which may be an array for placement over a relatively large skin surface, are provided with an good acoustic connection with the body structure of interest.

Traditional hydrogels used with traditional ultrasound probes are not able to provide the required adhesion for sustained and secure coupling to the skin.

SUMMARY OF THE INVENTION

Viewed from a first aspect, the present invention provides a tape for securing an ultrasound probe to the skin, the tape comprising a sonolucent silicone gel for transmitting ultrasound from an ultrasound transducer to the body.

The invention arises from the selection of silicone gel in place of the traditional hydrogel formulas. The silicone gel advantageously provides improved adhesion to typical ultrasound probe materials, which may be silicone rubber or the like, whilst also providing adhesion to the skin. Traditional ultrasound gels may not have the necessary properties for adhesion to an ultrasound probe, but instead are intended to be used with the operator holding the probe against the skin and in many cases sliding it across the skin, with adhesion therefore being a disadvantage.

By sonolucent it is meant that the gel is capable of transmitting ultrasound pulses without introducing significant interference, such that an acceptable acoustic response can be obtained from the body structure(s) of interest. For example, the desired outcome may be a sufficiently clear image for diagnostic purpose, or a measurement of blood flow velocity using Doppler ultrasound techniques. The materials used may be selected not only for their own sonic transmission capabilities, but also to reduce or remove echoes and/or interference created by the transition between the different gel and structural layers, between the gel and the body tissue, and/or between the gel and the probe surface. The gel formulations may be selected for their acoustic impedance in order to provide appropriate acoustic impedance matching with the adjacent skin or probe surface. As discussed below, it is preferred for special techniques to be used to produce a suitable sonolucent silicone gel.

The tape may include a first adhesive surface for adhesion of the silicone gel to the skin and a second adhesive surface for adhesion of the silicone gel to the ultrasound probe. The first and second adhesive surfaces are preferably surfaces of the silicone gel. There may be two silicone gel layers respectively providing the first and second adhesive surfaces. Two similar silicone gel layers may be used, or alternatively the layers may be of different types with properties optimised for best adhesion to the probe and to the skin, respectively.

Preferably the tape comprises a structural layer for supporting the gel layer(s). The structural layer comprises a sonolucent material and/or is sufficiently thin to have minimal effect on the sonolucency of the tape.

The structural layer may be in the form of a mesh or a mat of fibres. For example, fibres of a sonolucent polymer may be used. The use of fibres provides a good mechanical coupling between the structural layer and the gel layer(s). The voids in the mesh also allow direct coupling between the sonolucent gel on either side of the mesh.

However, in preferred embodiments a non-woven material is used for the structural layer, for example a thin layer of a material such as Reemay™, which is manufactured by and available from companies in the Fiberweb group (http://www.fiberweb.com).

The thickness of the tape may be in the range 100 to 500 µm, for example, about 400 µm. This thickness may be made up of two gel layers of preferably about equal thickness on either side of a structural layer as discussed above.

The silicone gel should be a skin compatible silicone adhesive. Medium to high tack compositions are preferably used. Examples of appropriate silicone adhesives are Silbione® RT Gel 4712 (medium tack) or RT Gel 4320 (high tack). Silbione® is a skin compatible silicone adhesive from Bluestar Silicones of New Jersey, USA. The 'tack' of the adhesive is a measure of how well it adheres and as the adherence varies with different surfaces tack is typically measured comparatively. One way of determining a tack value is a measurement of the energy needed to separate the adhesive from a surface when using a standard test set up, and these measurements are typically given in mJ/cm². For the above Silbione™ adhesives Bluestar Silicones use a test with a steel probe and an adhesive layer thickness of 0.25 mm, and provide tack values of 3.8 mJ/cm$^2$ for Silbione™ RT Gel 4712 (medium tack) and 6.6 mJ/cm$^2$ for Silbione® RT Gel 4320 (high tack). Preferred embodiments may utilise adhesives with tack values of 3 to 8 mJ/cm$^2$, measured using the test referred to above.

The adhesive surfaces may be provided with quick-release liners to protect them prior to application to the probe and the skin.

The sonolucent silicone tape should preferably not contain any air bubbles, as these will deteriorate the ultrasonic signal. The silicone adhesive may be treated to remove air bubbles or to prevent air bubble formation and hence the transfer tape preferably comprises silicone gel treated by degassing or other air bubble reduction treatment. This is not generally done in relation to silicone adhesives. Possible treatments are discussed below in relation to a method of manufacture provided by the invention.

The invention extends to the use of the tape for securing an ultrasound probe to the skin.

Viewed from a second aspect, the invention provides a method of manufacturing a silicone adhesive product comprising: treating the adhesive composition or components of the composition to remove air or prevent the formation of air bubbles, in order to provide a sonolucent adhesive product.

As noted above, prior art silicone adhesives are not treated in this way. The inventors have made the non-obvious realisation that silicone adhesives provided with the necessary sonolucency can be advantageously used for securing ultrasound probes to the skin.

A preferred treatment process comprises degassing the adhesive composition or components of the composition under vacuum. The vacuum may be a medium vacuum, i.e. a pressure in the range 0.3 bar to 1 mbar (30 kPa to 100 Pa). The example discussed in the preferred embodiment uses a pressure of about 15 mbar (1.5 kPa). Other alternative or additional techniques can also be used, such as the use of inhibitors in the silicone gel to delay the curing process until it reaches a "vacuum zone".

Typically, a silicone adhesive gel may be mixed using two or more components, and so a degassing or air bubble prevention treatment can be applied to each component before mixing. Mixing of components may be carried out under vacuum and/or with a specialised mixing device. Devices for mixing of two component epoxy resins have been found to be appropriate for small scale production, for example a Weicon mixing device such as the Weicon Hand Dispenser D50 and Weicon "Quattro" static mixer nozzle, available from Weicon GmbH & Co. KG. The silicone gel should be preferably be mixed without air present, e.g. under vacuum.

Preferred embodiments utilise the method for producing a tape product for adhesion of ultrasound probes to the skin. Hence the method advantageously comprises a step of transferring the adhesive composition onto a structural layer and/or into a mould, preferably without air present. Two layers of silicone gel may be applied to either side of a structural layer. The structural layer and the silicone gel composition may be as discussed above.

After degassing steps, the vacuum may be broken and the gel may be permitted to cure as usual to form a sonolucent silicone gel product.

The method of manufacture may utilise conventional techniques for transferring the adhesive to the structural layer and/or into a mould. Conventional films may be used to protect the adhesive during curing and/or for use as release liners to protect the adhesive before use.

It will be appreciated that the product of the above method is itself novel and hence the invention extends to a sonolucent silicone adhesive product obtainable or obtained by the manufacturing method set out above.

Viewed from a third aspect, the present invention provides an ultrasound probe apparatus for fixing to the skin, the apparatus comprising a probe surface for transmission of ultrasound pulses from transducers, wherein the probe surface comprises a roughened surface.

The use of a roughened surface on the probe surface acts to improve adhesion with an adhesive tape or the like, such as the tape of the first aspect. Whilst the tape of the first aspect provides an advance compared to prior art ultrasound coupling techniques, the inventors have found that improved strength of adhesion and adhesion for a longer period of time can be achieved when a roughened probe surface is used. This is especially the case when a gel layer of a standard composition selected for adhesion to the skin is also used for adhesion to the probe. The probe of this aspect advantageously provides improved adherence to conventional gel compositions as well as to the silicone based tape and other products described above.

Preferably, the roughened surface has a roughness equivalent to that achieved by sand blasting, in particular a roughness equivalent to that achieved by sand blasting a PVC surface, for example sand blasting at a pressure of 3 bar with a particle size of 220 μm. The roughened surface may hence be a sand blasted surface. A preferred material for the roughened surface is PVC. Alternative materials include polymethylmethacrylate (PMMA), acrylonitrile butadiene styrene (ABS), polystyrene, polyethylene (PE) or polycarbonate.

The roughened surface may be provided in the form of one or more areas of roughened material. Preferably a number of areas of roughened material are present on the probe surface. The area(s) of roughened material may be provided as a thin layer or film of material on top of the probe surface. Alternatively, the roughened material may be embedded in the probe surface. By the use of discrete roughened areas it is possible to avoid placing the roughened material over the ultrasound transducers, and hence the material used for the roughened surface is not limited in relation to its acoustic properties, and need not be sonolucent.

In a preferred embodiment, the probe surface is flexible and the probe comprises a flexible body, which holds ultrasound transducers of the probe at the desired angle to the probe surface. The ultrasound transducers may be for use in ultrasound Doppler measurement, for example measurement of blood flow velocity. Thus, the transducers may be affixed in the probe body at an angle to the probe surface suitable for Doppler ultrasound use. In alternative embodiments, the ultrasound transducers may be intended for measurement of acoustic impedance of adjacent tissue. In this case, the transducers may be affixed in the probe body at a right angle to the probe surface, such that the ultrasound is directed into the body perpendicular to the body surface where the probe is placed.

The use of a flexible probe ensures that the transducers can be effectively secured to the body even when the skin surface is curved or uneven. For example, it may be desirable to secure an array of transducers across a vein in the curved surface of a patient's arm to enable detection of possible extravasations as discussed above.

The body of the probe is preferably medical grade silicone. Silicone is particularly suited for adhesion to the silicone based adhesive described above. Alternatively, polyurethane may be used. The material of the body should be selected to provide the desired flexibility and should also be suitable for sanitisation and/or disinfection in order to allow use of the probe in a medical environment. The material may be suited for sterile production.

The roughened surface may be provided by material embedded within the body of the probe. Advantageously, a mould insert used to support the transducers within a mould for the body may also provide the roughened surface. This insert may be a blister formed to support the transducers. The mould insert may include projections or pads which extend toward the probe surface. By leaving surfaces of these projections exposed after the probe body is formed about the transducers and the mould insert, roughened areas can be easily provided. The insert is preferably PVC, which may be treated with sand blasting and application of a primer in order to form the desired roughness and to ensure good adhesion of the probe material, such as silicone, to the PVC.

In a preferred embodiment, the probe is adapted to curve in a single plane. Thus, the probe may be arranged to fit to a surface which approximates a cylinder. By restricting the flexibility of the probe to be mainly in a single direction, it is possible to obtain a greater flexibility in that direction without impairing operation of the transducers, which are typically rigid. For example, the probe may comprise a series of relatively rigid segments, each connected by flexible couplings. The relatively rigid segments may house rigid transducers, with flexible electrical connections passing through the flexible couplings.

Viewed from a fourth aspect, the present invention provides a method of manufacturing an ultrasound probe apparatus for fixing to the skin, the apparatus comprising a probe surface for transmission of ultrasound pulses from transducers, wherein the method comprises providing a roughened surface on the probe surface.

The roughened surface may be provided in a form as discussed above. The method may include roughening a material to use for the roughened surface. Preferably, the roughening step produces a roughness as is achieved by sand blasting, in particular a roughness equivalent to that achieved by sand blasting a PVC surface, for example at a pressure of 3 bar with a particle size of 220 μm. The roughening step may comprise sand blasting.

Preferably, the method includes securing the transducers in a mould insert, and moulding the probe body about the transducers and the insert. In this way, the transducers may be held at a desired angle to the probe surface during moulding. In a particularly preferred method, the insert comprises projections or pads that extend toward the probe surface and are exposed on the surface of the probe after moulding to form the roughened areas. The mould insert may be PVC as discussed above in relation to the third aspect.

In a preferred embodiment, the probe surface is flexible and the probe comprises a flexible body as discussed above.

Viewed from a fifth aspect the present invention provides an ultrasound probe apparatus for fixing to the skin, the apparatus comprising: a probe surface for transmission of ultrasound pulses from transducers, wherein the probe surface comprises a roughened surface; and a tape having a sonolucent gel layer for transmitting ultrasound from the ultrasound transducers to the body, a first adhesive surface for adhesion to the skin and a second adhesive surface for adhesion to the probe surface.

The combination of the tape with the roughened surface has been found to provide optimal adhesion of the probe to the skin, which allows ultrasound measurements such as those discussed above in relation to detecting extravasation and determining lung inspiration to be made effectively. The tape and probe may include optional features as discussed above.

In a preferred embodiment, the tape is sized to fit over the probe surface with a slight overlap. This ensures a good acoustic coupling between the transducers and the skin, and also enables the tape to be more easily removed from the skin and from the probe after use, as the overlap provides an area of tape which can be gripped easily. The overlap also allows for increased flexibility in placing the probe. The tape may be provided with a spacer to ensure correct positioning for the desired medical procedure. For example, where the probe is used to monitor extravasation as in WO 2004/052431 and WO 2009/044151 the tape may include a spacer extending away from the probe to set the distance between a point of injection and the probe location, which is downstream of the point of injection.

A sixth aspect of the invention provides a method of securing an ultrasound probe to the skin, the method comprising: providing a tape having a sonolucent gel layer, a first adhesive surface and a second adhesive surface; wherein the first adhesive surface is selected for adhesion to the skin and the second adhesive surface is selected for adhesion to a surface of the ultrasound probe; and providing a roughened surface on the probe surface.

This method may include features as discussed above.

The concept of an ultrasound probe formed by moulding a flexible material about ultrasound transducers is considered novel in its own right, and therefore in a seventh aspect, the present invention provides an ultrasound probe apparatus for fixing to the skin, the apparatus comprising a flexible body moulded about a plurality of ultrasound transducers, the transducers being permitted to move relative to one another such that a probe surface can conform to a contour of the body surface.

The use of a flexible probe ensures that the transducers can be effectively secured to the body even when the skin surface is curved or uneven. For example, it may be desirable to secure an array of transducers across a vein in the curved surface of a patient's arm to enable detection of possible extravasations as discussed above.

Preferably, the flexible body holds ultrasound transducers of the probe at the desired angle to the probe surface. The ultrasound transducers may be for use in ultrasound Doppler measurement, for example measurement of blood flow velocity. Thus, the transducers may be affixed in the probe body at an angle to the probe surface suitable for Doppler ultrasound use. In alternative embodiments, the ultrasound transducers may be intended for measurement of acoustic impedance of adjacent tissue. In this case, the transducers may be affixed in the probe body at a right angle to the probe surface, such that the ultrasound is directed into the body perpendicular to the body surface where the probe is placed.

The body of the probe is preferably medical grade silicone. Silicone is particularly suited for adhesion to the silicone based adhesive described above. Alternatively, polyurethane may be used. The material of the body should be selected to provide the desired flexibility and should also be suitable for sanitisation and/or disinfection in order to allow use of the probe in a medical environment. The material may be suited for sterile production.

In a preferred embodiment, the probe is adapted to curve in a single plane. Thus, the probe may be arranged to fit to a surface which approximates a cylinder. By restricting the flexibility of the probe to be mainly in a single direction, it is possible to obtain a greater flexibility in that direction without impairing operation of the transducers, which are typically rigid. For example, the probe may comprise a series of relatively rigid segments, each connected by flexible couplings.

The relatively rigid segments may house rigid transducers, with flexible electrical connections passing through the flexible couplings.

Viewed from an eighth aspect, the present invention provides a method of manufacturing an ultrasound probe apparatus for fixing to the skin, the apparatus comprising a flexible body and a plurality of ultrasound transducers, wherein the method comprises moulding body about the transducers such that the transducers are permitted to move relative to one by flexing of the body whereby a probe surface can conform to a contour of the body surface.

Preferably, the method includes securing the transducers in a mould insert, and moulding the probe body about the transducers and the insert. In this way, the transducers may be held at a desired angle to the probe surface during moulding.

These and other features of the present application and the resultant patent will become apparent to one of ordinary skill in the art upon review of the following detailed description when taken in conjunction with the several drawings and appended claims.

BRIEF DESCRIPTION OF THE DRAWINGS

Preferred embodiments of the present invention will now be described by way of example only and with reference to the accompanying drawings in which:

FIG. 4 shows a plan view, front elevation, side elevations and bottom view of a probe with tape attached, in this case the tape does not include a spacer.

DETAILED DESCRIPTION

Figure 1:
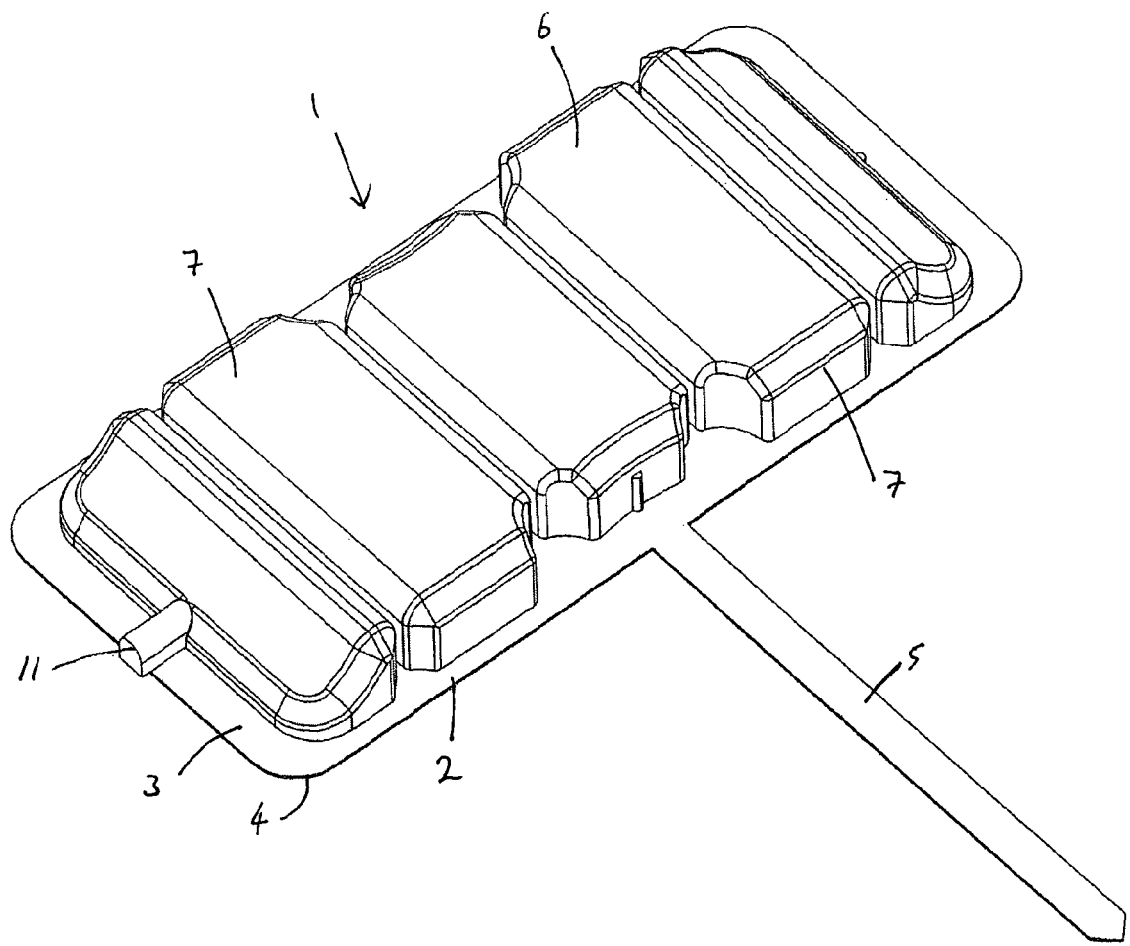
FIG. 1 illustrates a perspective view of a flexible probe apparatus and a corresponding tape, which has a spacer.
Figure 2:
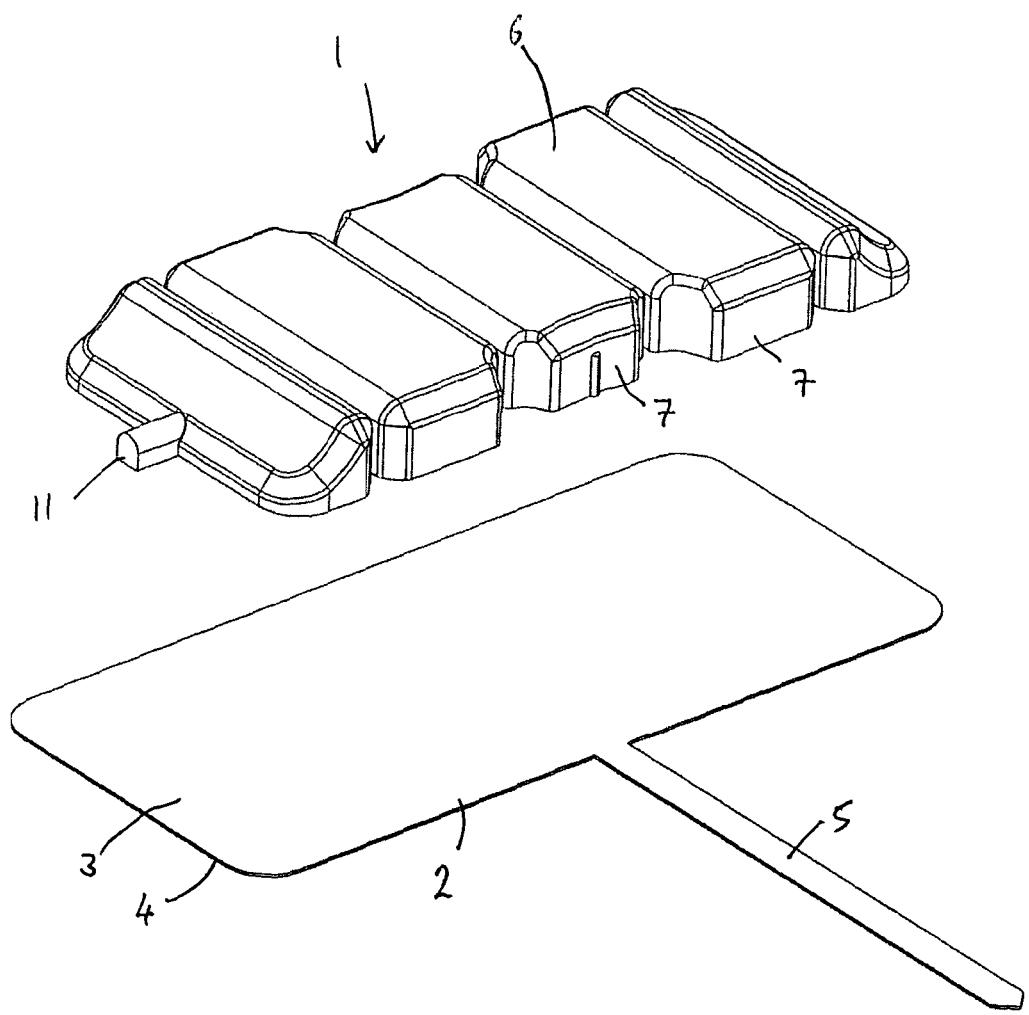
FIG. 2 shows the probe and tape of FIG. 1 in exploded view.

FIGS. 1 and 2 show an ultrasound probe 1 and tape 2 in perspective view, from above. The surface of the tape 2 that adheres to the skin is facing downward. The tape 2 is relatively thin, about 400 μm in the preferred embodiment. Tape thicknesses of between 200 to 500 μm may be used. The tape 2 comprises a first sonolucent gel layer 4, facing downward in FIGS. 1 and 2, and a second sonolucent gel layer 3. In the preferred embodiment, these layers are silicone adhesive adhered to a central sonolucent structural layer, which is preferably thin layer (e.g. 26 g/m$^2$) of a non-woven material such as Reemay™. In the embodiment of FIGS. 1 and 2, the tape 2 includes an optional spacer 5, which extends outward from the probe 1 by a set distance. The spacer 5 can be used to ensure correct placement of the probe and tape combination relative to a desired location on the body.

The preferred silicone based adhesive tape is manufactured using a Silbione™ skin compatible silicone adhesive as follows. The two components for the adhesive are degassed using at vacuum pressure, e.g. at 15 mbar (1.5 kPa) for 60 minutes, in order to remove trapped air. They should then be mixed, with a Weicon mixing device or similar device being used to minimise entrapped air. The mixed composition can be placed into a mould or applied to the non-woven material in a conventional fashion, with a PVA film, e.g. Solublon® of 40 μm thickness, being applied to protect exposed surfaces. A further degassing step should be applied to remove any entrapped air, e.g. at 15 mbar (1.5 kPa) for 15 minutes. The vacuum can then be broken and the adhesive cured as normal. The cured silicone adhesive should be placed in cold DI water and after 20 minutes the Solublon® film can be removed and replaced with a suitable release liner.

Further details of the probe 1 will now be described with reference to the figures. The probe 1 comprises a probe body 6, which is moulded from medical grade silicone, the details of which can be appreciated with additional reference to FIG. 3, which shows an explanatory view of the underside of the probe, and FIG. 4, which includes several views of a probe and tape combination. In the embodiment of FIG. 4, the tape 2 does not include the spacer 5. Omitting the spacer 5 makes the tape 2 a simpler shape, and hence easier to manufacture, but use of the probe 1 then requires a slightly higher degree of training for the operator to ensure correct placement.

The probe body 6 is made of a number of relatively rigid segments 7, with flexible coupling sections 8 between the segments 7. This construction enables the probe 1 to fit easily to a curved surface. The coupling sections 8 can be best seen in the side elevations of FIG. 4.

Figure 3:
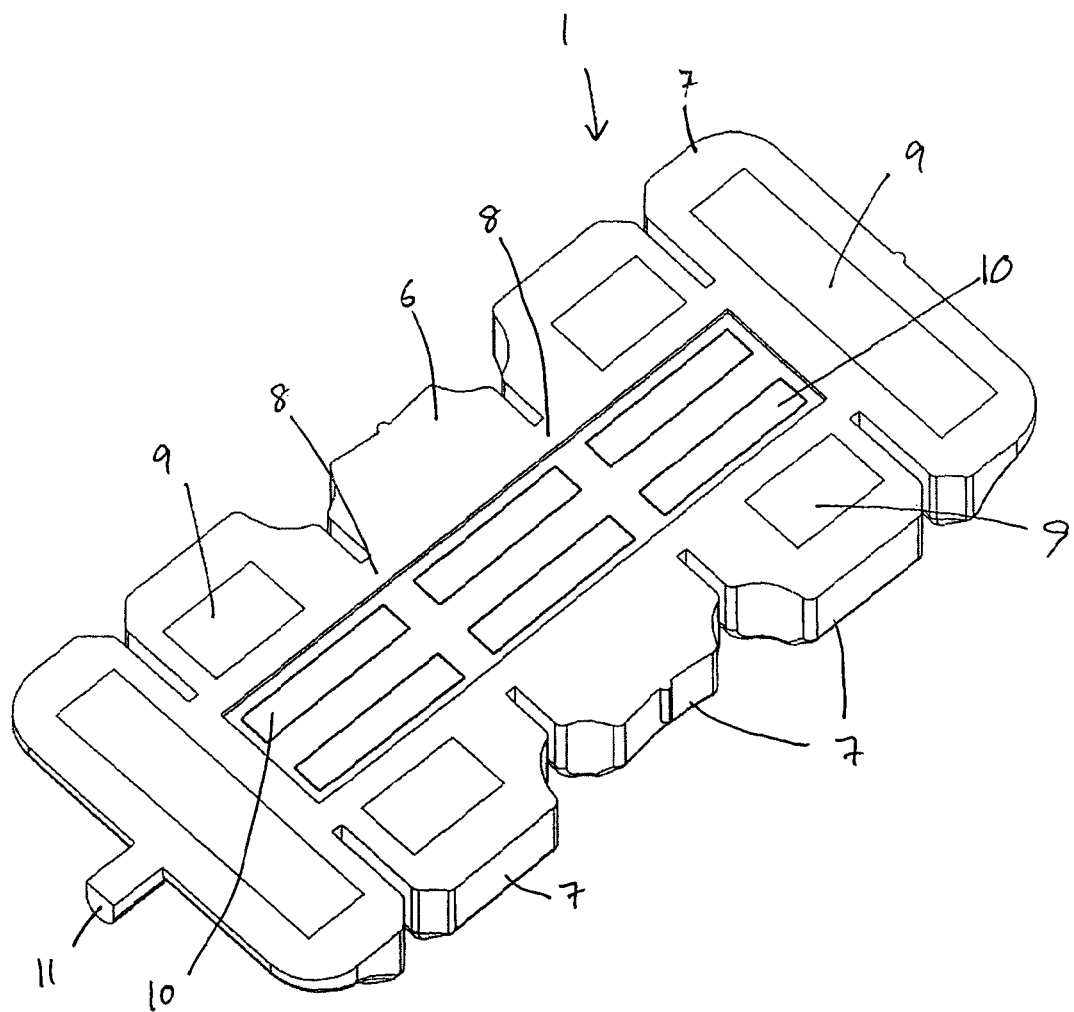
FIG. 3 is a perspective view of the underside of the probe.

On the underside of the probe 1 is a probe surface, which optionally includes a number of roughened areas 9. Although the silicone adhesive tape 2 will adhere sufficiently well to silicone surfaces of the probe body 6, the roughened areas 9 can be used to improve adhesion with the preferred silicone adhesive, and also provide improved adhesion with conventional hydrogel products. In the embodiment of FIG. 3 these roughened areas 9 are placed symmetrically about either end of the probe body 6. The probe surface is formed of the surface of the probe body 6 and is hence medical grade silicone. The roughened areas 9 are PVC that has been roughened by sandblasting.

The PVC is embedded within the probe body 6 and the roughened areas 9 are pads extending from a PVC mould insert, which is in the form of a blister formed around the transducer elements 10. The mould insert forms a "bed" for holding the transducer elements 10 during the silicone moulding process. The PVC insert ensures that the transducers 10 are then in the correct angle during moulding. The pads extend to the front face of the probe in order to form the roughened areas 9. A primer is applied to the PVC in order to allow for adhesion between the PVC and the medical silicone. The PVC insert is sandblasted prior to moulding in order to form the desired roughness. The mould insert is hinged in the coupling sections 8 in order to provide the requisite flexibility for the probe 1.

The probe 1 includes ultrasound transducers 10 embedded in the probe body 6. This embodiment includes three pairs of ultrasound transducers 10. It should be noted that the silicone probe surface extends over the ultrasound transducers 10, which are fully enclosed in the probe body 6 and would not be visible in normal use. FIG. 3 shows a rectangular section of the probe surface cut away in order to illustrate the location of the ultrasound transducers 10 in the probe body 6. As can be seen, the three pairs of transducers 10 are held in the three of the more rigid segments 7 with the flexible coupling sections 8 placed between the transducers 10. Electrical connections for the transducers pass through the flexible coupling sections 8, and electrical leads for connection to an ultrasound control apparatus are connected to the probe at electrical connecting point 11. The electrical leads can be integral to the probe, or a socket for connection with a jack plug or other electrical connector can be provided at the electrical connecting point 11.

The transducers 10 are supported in the probe body 6 at an appropriate angle for Doppler ultrasound measurements. This ensures that, in use, when the probe surface is adhered to the skin, the transducers 10 are automatically at the correct angle for making the desired Doppler ultrasound measurements. In alternative embodiments the transducers 10 can be supported in different orientations, dependant upon the type of ultrasound measurement that is required.

In use, the tape 2 is adhered to the probe 1 using the second sonolucent gel layer 3, which adheres to the probe surface and in particular to the roughened areas 9. The probe and tape combination is then adhered to the skin by means of the first sonolucent gel layer 4.

The tape 2 can be provided with protective non-adhesive layers that cover the first and second sonolucent gel layers. These protective non-adhesive layers are peeled off before use. The tape 2 can be provided in a roll or reel, and cut to size shortly before use.

Alternatively the tape 2 can be provided in pre-cut form, as a "pad" dimensioned to fit the probe 1. In this case the tape 2 is supplied in a suitable package. The top layer of the gel pad may also include a "frame". The frame can be a part of the gel pad on the upper side, and comprises a cage arranged to fit around the probe body and hold it against the pad. In use, the frame is lifted away from the pad to enable the probe to slide in between the adhesive surface and the frame. The frame can then be stuck back onto the pad in order to secure the placement of the probe and provide an additional means to prevent movement of the probe on the tape.

It is also envisaged that the tape 2 can be provided to the user already adhered to the probe 1. In this case the only first sonolucent gel layer 4 covered with a protective non-adhesive layer, which is removed before the probe and tape combination is adhered to the skin as one unit.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

We claim:

1. A system comprising an ultrasound probe and a tape for securing the ultrasound probe to the skin, wherein the ultrasound probe has a probe surface for transmission of ultrasound pulses from an ultrasound transducer, and wherein the tape is fixed to the probe surface and is arranged to adhere the probe surface to the skin, the tape comprising:
   a sonolucent adhesive silicone gel for transmitting ultrasound from the ultrasound transducer to the body;
   a first adhesive surface for adhesion of the silicone gel to the skin; and
   a second adhesive surface adhering the silicone gel to the probe surface of the ultrasound probe.

2. A system as claimed in claim 1, wherein the tape comprises a structural layer for supporting the gel layer(s).

3. A system as claimed in claim 2, wherein the structural layer is a non-woven material and there is a layer of silicone gel on either side of the non-woven material.

4. A system as claimed in claim 1, wherein the sonolucent silicone gel comprises silicone gel treated by vacuum degassing or other air bubble reduction treatment.

5. A method comprising:
   treating a silicone adhesive composition or components of the composition to remove air or prevent the formation of air bubbles, in order to provide a sonolucent adhesive product;
   transferring the treated adhesive composition onto a structural layer and/or a mould;
   curing the silicone to form a sonolucent silicone gel tape product; and
   fixing the sonolucent silicone gel tape product to an ultrasound probe, wherein the ultrasound probe has a probe surface for transmission of ultrasound pulses from an ultrasound transducer, and wherein the sonolucent silicone gel tape product is fixed to the probe surface and is arranged to adhere the probe surface to the skin.

6. A method as claimed in claim 5, wherein the treatment process comprises degassing the adhesive composition or components of the composition under vacuum.

7. A method as claimed in claim 5, wherein the silicone adhesive gel is a mixture of two or more components, and a degassing or air bubble prevention treatment is applied to each component before mixing.

8. A method as claimed in claim 7, comprising mixing the two components under vacuum and/or using a specialised mixing device to reduce air entrapment.

9. A system as claimed in claim 1, wherein the first adhesive surface and/or the second adhesive surface comprise a tack value of 3 to 8 $mJ/cm^2$.

10. A method as claimed in claim 5, wherein the cured silicone comprises a tack value of 3 to 8 $mJ/cm^2$.

* * * * *